United States Patent [19]

Albert

[11] Patent Number: 4,505,675
[45] Date of Patent: Mar. 19, 1985

[54] METHOD AND DEVICE FOR PREPARING ENDODONTIC FILLER

[76] Inventor: David C. Albert, 1800 Newell St., Alice, Tex. 78332

[21] Appl. No.: 443,570

[22] Filed: Nov. 22, 1982

[51] Int. Cl.³ .............................................. A61C 19/04
[52] U.S. Cl. ..................................................... 433/72
[58] Field of Search ........................... 433/72, 81, 224

[56] References Cited

U.S. PATENT DOCUMENTS 3,855,702 12/1974 Malmin ............................... 433/224
4,255,142 3/1981 Aoyagi ................................... 433/72

Primary Examiner—Robert Peshock
Attorney, Agent, or Firm—James J. Brown

[57] ABSTRACT

A method and device are described for preparing an endodontic filler for a root canal whereby the minimum diameter of the prepared root canal is determined and a filler for the root canal formed exterior to the canal so that it has a terminal diameter which corresponds to the minimum diameter of the prepared root canal and a shape which is appropriate for adaptation to the configuration of the canal. The invention further includes a gauge for forming the endodontic root canal filler and which comprises a unitary member having a plurality of calibrated, elongated, tapered cavities one of which is adapted to receive an elongated instrument which has the terminal diameter corresponding to the minimum diameter of the root canal. A second calibrated cavity has an appropriate form to receive the elongated instrument or a filler material and a linear scale corresponding to calibration on the first cavity.

2 Claims, 2 Drawing Figures

METHOD AND DEVICE FOR PREPARING ENDODONTIC FILLER

STATEMENT OF THE INVENTION

The present invention relates to a method and a device for preparing endodontic fillers for root canal therapy. More specifically, this invention relates to a system by which the minimum diameter of a prepared root canal is determined and a filler prepared having that minimum diameter and the proper taper as related to length, exterior to the root canal. Preparation of the root canal filler is accomplished using a gauge with tapered, calibrated cavities into which an elongated instrument having the same terminal diameter as the prepared root canal is inserted to indicate the appropriate minimum diameter for the filler.

BACKGROUND OF THE INVENTION

Root canal therapy requires that the infected root canal be cleaned to remove dead or diseased pulp and that the cavity thereby created in the root be filled with a material which fits tightly into the void space. Present techniques of root canal therapy essentially involve the initial cleaning of the canal using a series of small tapered files of increasing size to clear the canal. This procedure is then followed by the fitting and final insertion of the filler material into the canal. Frequently, the filler used for root canals is an elastomeric composition such as gutta percha which is supplied to the dentist in small tapered lengths of standard size which correspond generally to the size of the small tapered files that are used to clean the canal. These preformed fillers frequently however are not of exactly the right dimensions or configuration to provide the required exact fit in the canal and must therefore be trimmed by the operating dentist until the proper dimension is achieved to completely fill the excavated canal.

Present procedures for shaping and fitting root canal fillers involve essentially a trial and error operation in which the approximate length of the root canal is first determined by X-ray and by inserting into the infected canal the small tapered files used for cleaning, progressing to larger and larger files until the canal is completely free of necrotic debris. The standard filler is then marked at the same length as that portion of the file which was inserted into the canal. This procedures does not, however, always result in a filler having the appropriate lateral dimensions to fit the root canal and it is therefore frequently necessary to make further trimmings and adjustments until the exact fit is reached. All of this is difficult since the material being manipulated is flexible, and the procedure is time consuming for the dentist and therefore expensive for the patient.

A device for trimming different lengths of root canal filler is for example described in U.S. Pat. No. 4,255,142 to Aoyagi. U.S. Pat. No. 3,863,345 to Malmin also describes a system for root canal therapy which involves insertion of sealing material by means of an instrument into the excavated root canal.

OBJECTS OF THE INVENTION

It is an object of the present invention to provide a system for filling a root canal which avoids the tedious trial and error techniques of the prior art and permits the operating dentist to rapidly and accurately determine the proper dimensions for the root canal filler to be inserted into the root canal.

It is a further object of the present invention to provide a technique for preparing a root canal filler of proper dimensions outside of the root canal itself and without the need for repeatedly inserting and removing a filler material from the tooth until the proper fit is achieved.

Yet a further object of the present invention is to provide a device and a method for accurately determining the minimum width of the prepared root canal and then preparing a filler having the same dimensions and adapted to be inserted into the root canal to completely seal and fill the canal.

SUMMARY OF THE INVENTION

In accordance with the present invention a method and device are provided for quickly and accurately determining the proper dimensions of a prepared root canal and preparing filler material of the proper configuration and dimensions for filling this canal. Briefly, in accordance with the invention, a determination is first made of the minimum diameter of the tapered root canal cavity which has been prepared or cleaned using known techniques. Once this dimension is known, the root canal filler is measured to have the proper minimum diameter at some point along its taper and then the narrow tip is shortened to length.

Most conveniently, the present invention is carried out by determining the minimum diameter of the previously prepared root canal from an elongated instrument such as the last and therefore largest file which was used in the cleaning and preparation of the canal. The minimum diameter of this tapered instrument is the same as the minimum diameter of the tapered root canal. The filler material is then formed by inserting the tapered elongated instrument into a first calibrated tapered cavity so that the instrument engages the side walls of the cavity at a point corresponding to the minimum diameter of the instrument. A point corresponding to this point of engagement is then located on a second calibrated, tapered cavity having substantially the same taper as the instrument, and the filler material is then formed in this second cavity either by die-forming within the cavity or by removal and appropriate trimming of the filler tip to have the same minimum diameter, taper and relative length as does the root canal. In this manner, the filler material is actually shaped and formed to the proper dimensions exterior to the tooth and in such a way that an accurate fit is assured without the need for repeated trial and error adjustment as required by the prior art.

Figure 2:
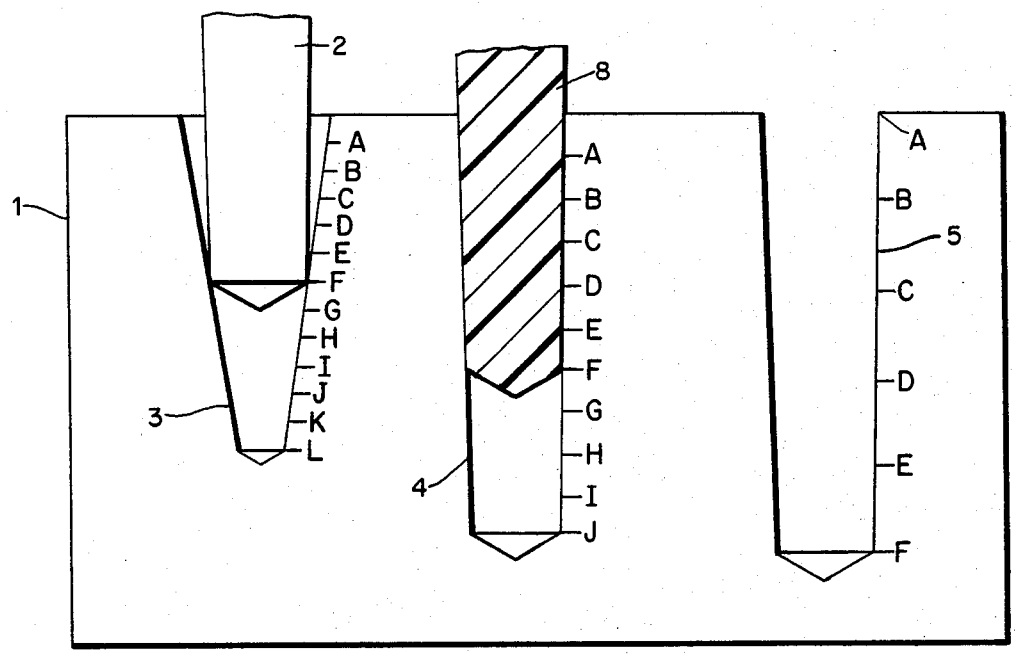
FIG. 2 is a frontal view of an additional embodiment of the device of the present invention.

The gauge which is conveniently employed in accordance with the present invention for forming the endodontic filler is illustrated in FIG. 2 of the drawings and comprises a series of calibrated, elongated tapered cavities in which the first cavity 3 is adapted to receive the elongated tapered instrument 2 used to prepare the root canal and which has the same minimum diameter as the prepared root canal. Conveniently, as shown for example in FIG. 2 of the drawings, the cavity 3 has a somewhat less acute taper than the instrument itself so that when the instrument is inserted into the cavity it engages the sides of the cavity at a point corresponding to the minimum diameter of the instrument and the root canal. The cavity is provided with calibration to facilitate determination of this minimum diameter. A second calibrated cavity 4 is provided having advantageously the same taper as the elongated instrument and being provided with calibration corresponding to that on the first cavity. Thus, the point on the second cavity having the same diameter as a point on the first cavity can easily be determined and it is to this point on the second cavity that the endodontic filler material 8 is adjusted so that it has a minimum diameter which corresponds to the minimum diameter of the prepared root canal. FIG. 2 of the drawings further illustrates a third cavity 5 which can optionally be provided to facilitate formation of the endodontic filler material.

Figure 1:
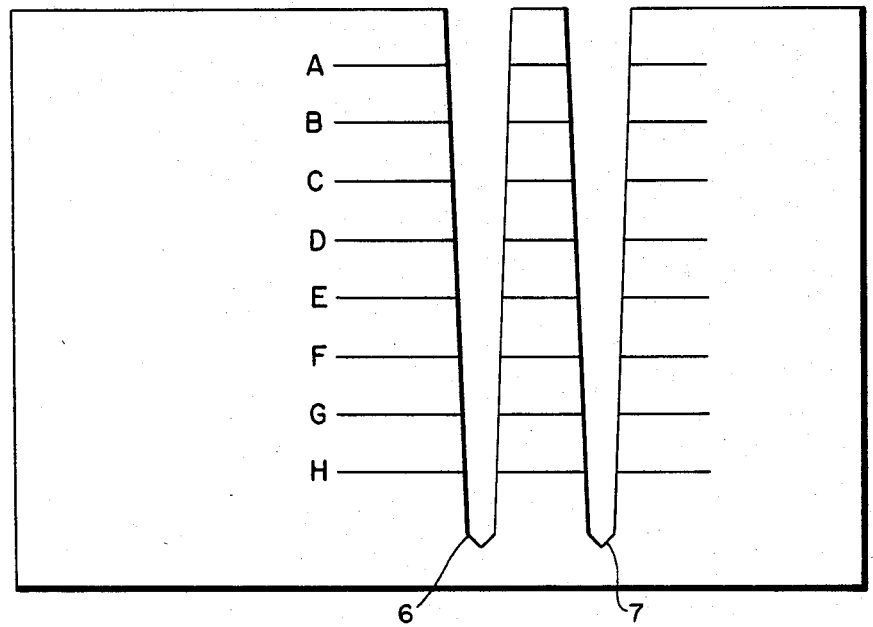
FIG. 1 is a frontal view of the device of the present invention.

FIG. 1 of the drawings illustrates an additional embodiment of the present invention wherein two identical tapered cavities 6 and 7 are provided the first being adapted to receive the elongated instrument or file used to prepare the root canal and being calibrated so that corresponding diameters are registered on the second cavity which is used to form the endodontic material. In use, the last instrument used to prepare the root canal is inserted into one of the cavities until it seats at the point where the sides are in contact with the sides of the tapered cavity. The scale which is marked to indicate instrument size or dimensions also indicates the appropriate dimensions for the filling material which is inserted into the second cavity and compared to the inserted instrument on the marked scale. If the filling material in the second cavity extends beyond the instrument when seated it may be shortened. If it is too short, the material can be formed inside the cavity to assume the proper dimensions. In either event, however, the present invention permits one to quickly and accurately form the filling material into the proper size and shape for filling the prepared root cavity without requiring continuous and tedious trial and error procedures of the prior art.

As an illustration of the invention, the device 1 shown in FIG. 2 of the drawings in which the first cavity 3 has an angle less acute than the endodontic file, the file contacts the side of the cavity at "F" on the graduated scale. The base diameter of the canal preparation is therefore known to be "F" which may be larger or smaller than the designated dimension of the instrument itself. The discrepancy can be due to manufacturing variations, instrument wear, compression or deformation. In accordance with the present invention the actual size of the prepared canal is, however, accurately indicated. The second cavity 4 can have the same taper as a standard instrument and the file can be inserted into the cavity to check diameter and taper. The filler material is placed into the same or an adjacent cavity to compare it to the final instrument dimension. The pliant filler can be compressed into the receptacle to form it to proper dimensions and any excess length of filler can be trimmed away as indicated by the graduated scale. Since the procedure of the present invention is not performed inside a surgically open tooth, a dental assistant rather than a doctor may perform the preliminary fittings of the filler material.

The gauge device having the tapered cavities which is used in accordance with the present invention can be constructed of a clear block material having the requisite size cavity drilled or cast into it, and the calibration scale marked within the medium or on the outside. Alternatively, it is not necessary that the cavities be completely conical; they can, for example, merely be tapered slots cut in a sheet of material.

What is claimed is:

1. A gauge for forming an endodontic filler for a root canal external to said root canal which comprises a unitary member having a plurality of calibrated, elongated, tapered cavities, the first said cavity being adapted to receive an elongated instrument having a terminal diameter corresponding to the minimum diameter of said root canal and precisely fitting therein, said instrument when inserted into said cavity being positioned to engage the side thereof to register the point on the wall of said cavity corresponding to the minimum diameter of said root canal, the second calibrated cavity having an appropriate form to receive said instrument or a filler material, and having a linear scale corresponding to the calibration on said first cavity and adapted to indicate the point on said second cavity corresponding to said minimum diameter of the root canal.

2. A method for preparing an endodontic root canal filler exterior to said canal, which comprises determining the minimum diameter of a prepared root canal from an elongated instrument having the same terminal diameter as the minimum diameter of said prepared canal and fitting precisely therein, and forming exterior to said canal said endodontic filler by inserting said elongated instrument into a first calibrated tapered cavity in a member gauge so that said instrument engages the sidewalls of the cavity at a point corresponding to the terminal diameter of said instrument, determining said point of engagement and locating on a second calibrated, tapered cavity in said gauge member having substantially the form desired of the filler, the corresponding point where the diameter of said cavity corresponds to said terminal diameter of said instrument, and shaping in said second cavity an elongated filler having a terminal diameter corresponding to the minimum diameter of the prepared root canal.

* * * * *